United States Patent [19]
Border

[11] Patent Number: 5,824,655
[45] Date of Patent: Oct. 20, 1998

[54] ANTI-TRANSFORMING GROWTH FACTOR-β GENE THERAPY

[75] Inventor: Wayne A. Border, Salt Lake City, Utah

[73] Assignee: The University of Utah, Salt Lake City, Utah

[21] Appl. No.: 389,887

[22] Filed: Feb. 15, 1995

[51] Int. Cl.⁶ ...................................................... A01N 43/04
[52] U.S. Cl. ........................ 514/44; 424/93.7; 424/93.21; 514/2; 800/2; 435/352; 435/353; 435/354; 435/366; 435/320.1; 435/172.3
[58] Field of Search ................................ 424/93.7, 93.21; 935/54; 514/2, 44; 800/2; 435/240.1, 240.2, 172.3, 320.1, 91.1, 93.1, 352, 353, 354, 366

[56] References Cited

FOREIGN PATENT DOCUMENTS

| | | |
|---|---|---|
| WOA91 10727 | 7/1991 | WIPO . |
| WOA92 17206 | 10/1992 | WIPO . |
| WOA93 09228 | 5/1993 | WIPO . |
| WOA93 10215 | 5/1993 | WIPO . |
| 9310808 | 6/1993 | WIPO . |
| WOA93 21945 | 11/1993 | WIPO . |

OTHER PUBLICATIONS

Yamaguchi et al, Nature, vol. 336, pp. 244–246 17 Nov. 1988.
Gutierrez et al, The Lancet, vol 339: Mar. 21, 1992, pp. 715–721.
Friedmann, Cancer (Supp), Sep. 1992, vol. 70(6) pp. 1810–1818.
Marshall, Science, 269:1050–1055, 1995.
Miller et al., FASEB J. 9:190–199, 1995.
Culver et al., TIG 10(5):174–178, 1994.
Hodgson, Exp Opin. Ther. Pat., 5(5):459–469, 1995.
NIH, "Report and Recommendations", Dec. 7, 1995, 1–40.
Yamamoto et al., May 22, 1987, "Quantitative and qualitative studies of antibody–induced mesangial cell damage in the rat," *Kidney International* 32:514–525.
Bagchus, et al., 1986, "Glomerulonephritis Induced by Monoclonal Anti–Thy 1.1 Antibodies," *Laboratory Investigation* 55:680–687.
Border, 1988, "Distinguishing minimal–change disease from mesangial disorders," *Kidney International* 34:419–434.
Isaka et al., 3, Sep. 1995, "Decorin Gene Therapy for Experimental Glomerulonephritis," *J. Am. Soc. Nephrol* 6:897.
Fitzpatrick et al., 1994, "Transforming Growth Factor–Beta: Antisense RNA–Mediated Inhibition Affects Anchorage–Independent Growth, Tumorigenicity and Tumor–Infiltrating T–Cells in Malignant Mesothelioma," *Growth Factors* 11:29–44.

Wolfe, Jon A. et al., "Direct Gene Transfer into Mouse Muscle in Vivo." *Science* 247:1465–1468 (1990).
Kaneda, Yasufumi et al., "Increased Expression of DNA Cointroduced with Nuclear Protein in Adult Rat Liver." *Science* 243:375–378 (1989).
Kato, Keiko et al., "Expression of Hepatitis B Virus Surface Antigen in Adult Rat Liver." *J. Biol. Chem.* 266:3361–3364 (1991).
Nakanishi, Mahito et al., "Efficient Introduction of Contents of Liposomes into Cells Using HVJ (Sendai Virus)." *Exp. Cell Res.* 159:399–409 (1985).
Yamaguchi, Yu et al., "Negative Regulation of Transforming Growth Factor–β by the Proteoglycan Decorin." *Nature* 346:281–284 (1990).
Border, Wayne A. et al., "Natural Inhibitor of Transforming Growth Factor–β Protects Against Scarring in Experimental Kidney Disease." *Nature* 360:361–364 (1992).
Border, Wayne A. et al., "Suppression of Experimental Glomerulonephritis by Antiserum Against Transforming Growth Factor β1." *Nature* 346:371–374 (1990).
Morishita, Ryuichi et al., "Intimal Hyperplasia After Vascular Injury is Inhibited by Antisense cdk 2 Kinase Oligonucleotides." *J. Clin. Invest.* 93:1458–1464 (1994).
Kahari, Veli–Matti et al., "Differential Regulation of Extracellular Matrix Proteoglycan (PG) Gene Expression." *J. Biol. Chem.* 266:10608–10615 (1991).
Takeshita, Satoshi et al., "Increased Gene Expression after Liposome–Mediated Arterial Gene Transfer Associated with Intimal Smooth Muscle Cell Proliferation." *J. Clin. Invest.* 93:652–661 (1994).
Okuda, Seiya et al., "Elevated Expression of Transforming Growth Factor–β and Proteoglycan Production in Experimental Glomerulonephritis." *J. Clin. Invest.* 86:453–462 (1990).
Border, Wayne A. and Ruoslahti, Erkki "Transforming Growth Factor–β in Disease: The Dark Side of Tissue Repair," *J. Clin. Invest.* 90:1–7 (1992).

(List continued on next page.)

*Primary Examiner*—Christopher S. F. Low
*Attorney, Agent, or Firm*—Mandel & Adriano

[57] ABSTRACT

The present invention provides methods for reducing a pathology in a subject characterized by a deleterious accumulation of TGF-β-induced extracellular matrix in a tissue by introducing a nucleic acid encoding a TGFβ-specific inhibitory agent or active fragment thereof into a cell in the subject. In one embodiment, the nucleic acid encoding the TGF-β specific inhibitory agent is introduced into a cell in vivo by injection, for example, in skeletal muscle. In another embodiment, the nucleic acid encoding the TGF-β specific inhibitory agent is transfected into a cell ex vivo to obtain a cell expressing the agent, and the cell is then administered into the subject to be treated. TGF-β specific inhibitory agents of the present invention include, but are not limited to, members of the decoring family of proteoglycans such as decorin, biglycan, fibromodulin and lumican or an antibody specific for TGF-β. Pathologies that can be reduced by the present invention include various fibrotic diseases and conditions.

7 Claims, 3 Drawing Sheets

OTHER PUBLICATIONS

Isaka, Yoshitaka et al., "Glomerulosclerosis Induced by In Vivo Transfection of Transforming Growth Factor-β of Platelet–derived Growth Factor Gene into the Rat Kidney." *J. Clin. Invest.* 92:2597–2601 (1993).

Westergren–Thorsson, Gunilla et al., "Altered Expression of Small Proteoglycans, Collagen, and Transforming Growth Factor-$\beta_1$ in Developing Bleomycin–induced Pulmonary Fibrosis in Rats." *J. Clin. Invest.* 92:632–637 (1993).

Yamamoto, Tatsuo et al., "Sustained Expression of TGF–β1 Underlies Development of Progressive Kidney Fibrosis." *Kidney Int.* 45:916–927 (1994).

Border, Wayne A. and Noble, Nancy A., "Transforming Growth Factor β in Tissue Fibrosis." *New England J. of Med.* 331:1286–1292 (1994).

Takeuchi, Yasuhiro et al., "Bone Matrix Decorin Binds Transforming Growth Factor–β and Enhances Its Bioactivity." *J. Biol. Chem.* 269:32634–32638 (1994).

Funderburgh et al., "Sequence and Structural Implications of a Bovine Corneal Keratin Sulfate Proteoglycan Core Protein: Protein 37B Represents Bovine Lumicon and Proteins 37 A aaand 25 Are Unique." *J. Biol. Chem.* 268:11874–11880 (1993).

Takahashi et al., "Keratin Sulfate and Dermatin Sulfate Proteoglycans Associate with Type VI Collagen in Fetal Rabbit Cornea." *J. Histochem. Cytochem.* 41:1447–1457 (1993).

Blochberger et al., "Isolation and Partial Characterization of Lumicon and Decorin From Adult Chicken Cornea." *J. Biol. Chem.* 267:20613–20619 (1992).

Niwa, et al., "Efficient Selection for High–Expression Transfectants with a Novel Eukaryotic Vector." *Gene* 108:193–199 (1991).

Antonsson et al., "Structure and Deduced Amino Acid Sequence of the Human Fibromodulin Gene." *Biochem. Biophys. Acta.* 1174:204–206 (1993).

Fisher et al., "Deduced Protein Sequence of Bone Small Proteoglycan I (biglycan) shows Homology with Proteoglycan II (Decorin) and Serveral Nonconnective Tissue Proteins in a Variety of Species." *J. Biol. Chem.* 264:4571–4575 (1989).

Fukushima et al., "Localization of Transforming Growth Factor Beta Binding Site in Betaglycan. Comparison With Small Extracellular Matrix Proteins." *J. Biol. Chem.* 268:22710–22715 (1993).

Lopez–Casillas et al., "Structure and Expression of the Membrane Proteoglycan Betaglycan, a Component of the TGF–β Receptor System." *Cell* 67:785–795 (1991).

St–Jacques et al., Molecular Characterization and in Situ Localization of Murine Endoglin Reveal that it is a Transforming Growth Factor–Beta Binding Protein of Endothelial and Stromal Cells. *Endocrinology* 134:2645–2657 (1994).

Krusius and Ruoslahti, "Primary Structure of an Extracellular Matrix Proteoglycan Core Protein Deduced from Cloned cDNA." *Pro. Natl. Acad. Sci. USA* 83:7683–7687 (1986).

FIG. 4A
DECORIN TRANSFECTION

FIG. 4B
CAT TRANSFECTION

ANTI-TRANSFORMING GROWTH FACTOR-β GENE THERAPY

The present invention was supported in part by Grant DK43609 from the National Institute of Diabetes and Digestinal and Kidney Diseases. The U.S. government may have certain rights in this invention.

BACKGROUND OF INVENTION

1. Field of the Invention

This invention relates generally to the regulation of growth factors and, more specifically, to the control of excessive extracellular matrix production and cell growth influenced by the growth factor TGF-β.

2. Background Information

Progressive fibrosis of the kidney, liver, lung, heart, bone marrow, and skin is both a major cause of suffering and death and an important contributor to the cost of health care. Advances in cell and cytokine biology have brought a new understanding of the molecular events underlying tissue fibrosis. It has become clear that the development of fibrosis is no longer viewed as a unique pathological process but is viewed instead as an excess of the same biologic events involved in normal tissue repair.

A central event in tissue repair is the release of cytokines in response to injury. Transforming growth factor-β (TGF-β) is a prototypical cytokine that plays a key role in the initiation and termination of tissue repair by stimulating cell proliferation and production of extracellular matrix material. The extracellular matrix is a complex superstructure of self-aggregating macromolecules, including fibronectin, collagens, and proteoglycans, to which cells attach by means of surface receptors. Integrins are a class of surface receptors known to bind specific matrix components. Matrix surrounding the cells is maintained by a dynamic process of degradation of existing matrix and synthesis and reformation of new matrix. TGF-β is one factor involved in the regulation of matrix accumulation, both stimulating new matrix synthesis and inhibiting matrix degradation.

Tissue fibrosis is a pathological state characterized by a deleterious accumulation of extracellular matrix. For example, in progressive glomerular disease of the kidney, extracellular matrix accumulates in the mesangium or along the glomerular basement membrane, eventually causing end-stage disease and uremia. Similarly, adult or acute respiratory distress syndrome (ARDS) involves a deleterious accumulation of matrix materials in the lung, while cirrhosis of the liver is characterized by a deleterious matrix accumulation evidenced by scarring of the liver. Another condition characterized by the deleterious accumulation of extracellular matrix is diabetes, which is now the most common cause of progressive kidney failure.

Uncontrolled synthesis of TGF-β is one factor which caused the deleterious accumulation of extracellular matrix that underlies the development of tissue fibrosis. Methods to control the action of TGF-β will have a significant impact on the treatment and prevention of tissue fibrosis and on the overall cost of health care.

Thus, a need exists to provide new approaches for treating tissue fibrosis resulting from TGF-β-induced accumulation of extracellular matrix. The present invention satisfies this need and provides related advantages as well.

SUMMARY OF THE INVENTION

The present invention provides methods for reducing a pathology in a subject characterized by a deleterious accumulation of TGF-β-induced extracellular matrix in a tissue by introducing a nucleic acid encoding a TGFβ-specific inhibitory agent or active fragment thereof into a cell in the subject.

In one embodiment, a nucleic acid encoding the TGF-β specific inhibitory agent is introduced into a cell in vivo by injection, for example, in skeletal muscle. In another embodiment, the nucleic acid encoding the TGF-β specific inhibitory agent is transfected into a cell ex vivo to obtain a cell expressing the agent, and the cell is then transplanted or grafted into the subject to be treated.

Cells that can express the TGF-β specific inhibitory agent include those from skeletal muscle, kidney, liver, lung and skin.

TGF-β specific inhibitory agents of the present invention include, for example, members of the decorin family of proteoglycans such as decorin, biglycan, fibromodulin and lumican, TGF-β specific receptors such as betaglycan and endoglin, and antibodies specific for TGF-β.

Pathologies that can be reduced by the present invention include, but are not limited to, fibrotic diseases and conditions, such as glomerulonephritis, ARDS, cirrhosis, fibrotic cancer, fibrosis of the lungs, arteriosclerosis, post myocardial infarction, cardiac fibrosis, post-angioplasty restenosis, renal interstitial fibrosis, scarring and diabetes-associated pathologies. Tissues that can be treated by the invention include kidney, liver, lung or skin.

The invention also provides methods for reducing a pathology in a subject characterized by TGF-β-induced deleterious growth of a tissue. The method consists of introducing a nucleic acid encoding a TGF-β specific inhibitory agent or an active fragment thereof in a cell in the subject, wherein the specific agent or active fragment thereof is expressed in the cell, resulting in suppression of the deleterious growth of the tissue. Expression of the TGF-β specific inhibitory agent can be achieved by direct injection of the nucleic acid encoding the agent in vivo or by transfection of a cell ex vivo and then transplanting or grafting the transfected cell into a subject.

BRIEF DESCRIPTION OF THE DRAWINGS

FIGS. 3A and 3B show reduced expression of TGF-β in glomerulonephritic rats injected intramuscularly with a decorin expression vector. FIG. 3A is a northern blot of glomerular mRNA isolated from the kidneys of glomerulonephritic rats sacrificed 6 days after injection of a rat decorin expression vector (lane 1) or a chloramphenicol acetyl-transferase expression vector (lane 2). The 2.5 kilobase (kb)

marker represents hybridization with a decorin specific probe while the 1.3 kb marker represents hybridization with a glyceraldehyde phosphate dehydrogenase (GAPDH) specific probe.

FIGS. 4A to 4F show decreased accumulation of extracellular matrix components in glomeruli of nephritic kidneys following intramuscular injection of a decorin expression vector.

DETAILED DESCRIPTION OF THE INVENTION

The invention is directed to methods for reducing a pathology characterized by the TGFβ-induced deleterious accumulation of extracellular matrix in a tissue. Such methods involve introducing a nucleic acid encoding a TGFβ-specific inhibitory agent into a cell in a subject, resulting in expression of the agent in the subject. The methods are advantageous over other modes of administration because sustained production of the inhibitory agent can be accomplished by modifying an endogenous cell to express its encoding nucleic acid.

In one embodiment, a nucleic acid encoding the TGF-β specific inhibitory agent decorin is available in an expression vector. The decorin encoding vector is injected intramuscularly into a subject having a fibroproliferative disease such as glomerulonephritis. To ensure sufficient transfection efficiency at the site of injection, the decorin encoded vector is encapsulated into a hemagglutinating virus of Japan (HVJ) liposome construct. Following injection, decorin is expressed and secreted into the circulation where it accumulates in the kidney. As a TGF-β specific inhibitory agent, decorin can bind to TGF-β at the site of disease and inhibit the deleterious accumulation of extracellular matrix.

As used herein, the term "ITGF-β specific inhibitory agent" is intended to mean a protein or active fragment thereof that can inhibit activities of TGF-β, which are associated with fibroproliferative diseases. One TGF-β activity associated with fibroproliferative diseases is the induction or accumulation of extracellular matrix. Another TGF-β activity associated with such diseases is the induction of cell proliferation. TGF-β specific inhibitory agents are therefore capable of inhibiting either or both of these activities.

Decorin is an example of a TGF-β specific inhibitory agent that can be used to treat fibrotic diseases and fibrotic conditions. Other examples of TGF-β specific inhibitory agents include, but are not limited to the decorin family of molecules such as biglycan, fibromodulin and lumican, TGF-β receptors such as betaglycan and endoglin and soluble forms and active fragments thereof and antibodies specific for TGF-β. A TGF-β specific inhibitory agent also includes a nucleic acid encoding a particular TGF-β specific inhibitory agent. When the TGF-β specific inhibitory agents are such encoding nucleic acids, the activity of TGF-β is inhibited by, for example, expressing the encoded agent in a cell in a subject.

As used herein, "decorin" refers to a proteoglycan having substantially the structural characteristics defined in Krusius and Ruoslahti (*Pro. Natl. Acad. Sci. (USA)* 83:7638-(1986), which is incorporated herein by reference, and functional equivalents thereof. Human fibroblast decorin having substantially the amino acid sequence presented in Krusius and Ruoslahti (supra), refers both to the native composition and to modifications thereof that substantially retain the functional characteristics of the molecule, such as the ability to inhibit the activity of TGF-β. The core protein of decorin, which is the decorin polypeptide without attached glycosaminoglycan, is also included within the meaning of decorin as defined herein. Decorin can be rendered glycosaminoglycan-free by enzymatic treatment, mutation or other means, such as by producing recombinant decorin in cells incapable of attaching glycosaminoglycan chains to a core protein. As described above, both decorin and decorin core protein are examples of TGF-β specific inhibitory agents.

Functional equivalents of decorin include modifications of decorin that retain functional characteristics of decorin such as the ability to inhibit the activity of TGF-β. Modifications can include, for example, the substitution or addition of one or more amino acids that do not interfere with the TGF-β specific inhibitory activity of the decorin core protein. In addition, functional equivalents of decorin also include the members of the decorin family of proteoglycans, such as biglycan, fibromodulin and lumican, that share a structural and a functional relationship with decorin (Funderburgh et al., *J. Biol. Chem.* 269:11874–11880 (1993), Takahashi et al., *J. Histochem. Cytochem.* 41:1447–1457 (1993), Yamaguchi et al., *Nature* 346:281–284 (1990) and Blockberger et al., *J. Biol. Chem.* 267:20613–20619 (1992), each of which are incorporated herein by reference.

As used herein, the term "active fragment" is intended to mean a portion of a full length TGF-β specific inhibitory agent, provided that the portion has the TGF-β activity characteristic of the corresponding full length protein. Thus, an active fragment is capable of preventing the induction or deleterious accumulation of extracellular matrix in a tissue. Active fragments of decorin that can inhibit binding of TGF-β to decorin or a cell are known in the art (see WO 93/20202, which is incorporated herein by reference in its entirety). For example, a fusion protein that encompasses the amino terminal 45 residues of decorin, including a mutation of cysteine residue 26 to a tyrosine, can inhibit the activity of TGF-β (see WO 93/20202). Other active fragments of decorin or other TGF-β specific inhibitory agents are known or can be determined by one skilled in the art.

The present invention can be used to reduce a pathology characterized by a deleterious accumulation of extracellular matrix. A variety of diseases are characterized by deleterious accumulation of extracellular matrix involving collagens, fibronectin and other matrix components. Such diseases include, for example, glomerulonephritis, adult or acute respiratory distress syndrome (ARDS), diabetes-associated pathologies, such as diabetic kidney disease, fibrotic diseases of the liver and lung and post infarction cardiac fibrosis. Also included are fibrocytic disease, fibrosclerosis, as well as fibrotic cancers, such as of the breast, uterus or pancreas, including fibroids, fibroma, fibroadenomas and fibrosarcomas.

In addition, there are a variety of medical conditions associated with a deleterious accumulation of extracellular matrix involving increased collagens, fibronectin and other matrix components. Such conditions include, for example, post myocardial infarction, cardiac fibrosis and post-angioplasty restenosis and renal interstitial fibrosis, excessive scarring such as keloid scars and scars resulting from injury, burns, or surgery.

As used herein, the term "reducing a pathology" means a reduction in at least one characteristic associated with the pathology. For example, glomerulonephritis can be characterized by pathologies such as sclerosis resulting from an increase in extracellular matrix or hypercellularity, resulting in loss in kidney function. Therefore, a decrease in sclerosis following treatment of glomerulonephritis with the present invention is a reduction in a pathology as defined herein.

The diseases and conditions disclosed herein as having a deleterious accumulation of extracellular matrix are sufficiently similar in pathology to be included into the general categories known as fibrotic diseases or fibrotic conditions. There is now overwhelming evidence that TGF-β is an important causative factor in these diseases and conditions, both from animal models of human diseases and in human diseases (for review see Border and Ruoslahti, *J. Clin Invest.* 90:1–7 (1992) and Border and Noble, *New Engl. J. Med.* 331:1286–1292 (1994), both of which are incorporated herein by reference). TGF-β mediates these pathologies by stimulating production of collagens, fibronectin, and other matrix components, and, in part by stimulating proliferation of mesenchymal cells in the tissue. The proliferation of mesenchymal cells results in a deleterious accumulation of extracellular matrix produced by the expanding cells that obliterates the parenchymal tissue thereby destroying organ function.

The methods of the present invention can be used to treat or prevent such pathologies in a subject by expressing a TGF-β specific inhibitory agent in the subject. Although the invention is directed to methods that reduce the deleterious accumulation of extracellular matrix by inhibiting TGF-β with TGF-β specific inhibitory agents, the mechanism by which such agents work is unimportant. For example, the TGF-β specific inhibitory agent can directly inhibit TGF-β by binding to TGF-β and preventing it from binding to its receptors or, such agent can indirectly inhibit the activity of TGF-β by, for example, inhibiting the synthesis or secretion of TGF-β or by sequestering TGF-β away from target cells. In addition, the pathologies disclosed as a group herein are merely representative and a person skilled in the art would readily recognize that the methods of the present invention are useful in any pathology associated with deleterious accumulation of extracellular matrix.

TGF-β is a multifunctional cytokine that normally regulates repair and regeneration following tissue injury. During normal tissue repair, TGF-β production is increased to stimulate the process of repair and when completed, TGF-β expression is reduced. If TGF-β expression is not reduced following normal tissue repair, then fibrosis can develop. Thus, repeated tissue injury or a defect in TGF-β regulation leading to sustained TGF-β production results in deleterious accumulation of extracellular matrix underlying tissue fibrosis (Border and Noble, supra).

TGF-β is synthesized as a 391 amino acid precursor molecule that is proteolytically cleaved to yield peptide fragments and a 112 amino acid subunit. Active TGF-β is a 25 kilodalton (kD) dimeric protein composed of two 112 amino acid subunits linked by a disulfide bond. TGF-β is secreted in an inactive or latent form that requires activation before it can exert biological effect. The latent form of TGF-β is a high-molecular weight complex formed between the TGF-β dimer and a cleavage fragment of the precursor TGF-β, known as latency associated peptide. Latent TGF-β is stored at the cell surface and in the extracellular matrix and is converted to active TGF-β by an unknown mechanism.

While not wishing to be held by this explanation, the ability of TGF-β to stimulate production of collagens, fibronectin and other matrix proteins is mediated through binding of specific cell surface receptors. TGF-β has been demonstrated to bind three membrane proteins, referred to as receptors types I, II and III, which are present on virtually all types of cells. The type I and type II receptors contain transmembrane serine-threonine kinase domains that interact and facilitate intracellular signalling. The type III receptor, also known as betaglycan, is a membrane-anchored proteoglycan that facilitates recognition of TGF-β by the type I and type II receptors. The effects of TGF-β on the synthesis and deposition of extracellular matrix components are mediated by the type I receptor, while effects on cell proliferation are mediated by the type II receptor.

The effects of TGF-β on cell proliferation are complex, but a useful generalization is that the proliferation of mesenchymally-derived cells is generally stimulated by TGF-β, whereas epithelial cells are inhibited in their growth. TGF-β also stimulates extracellular matrix production in mesenchymally-derived cells (Okuda et al., *J. Clin. Invest.* 86:453–462 (1990), which is incorporated herein by reference) and this also can be inhibited with decorin (Border et al., supra). Several types of cancer cells and tumors are dependent on TGF-β activity for tumor growth. Examples include a mouse mesothelial tumor that faithfully reproduces the features of the corresponding human malignancy (Fitzpatrick, et al., *Growth Factors* 11:29 (1994)), a fibrosarcoma (Spearman et al., *Gene* 149:25 (1994)) and Chinese hamster ovary cells (Yamaguchi and Ruoslahti, *Nature* 336:244–246 (1988). Tumor growth in these models was shown to be linked to elevated TGF-β by suppressing TGF-β activity with antisense oligonucleotides.

TGF-β specific inhibitory agents of the present invention have been used successfully to inhibit the development of acute mesangial proliferative glomerulonephritis induced by TGF-β in an animal model (see Examples I and IV). Glomeruli from rats made nephritic by intravenous injection of antithymocyte serum are characterized by an increased synthesis of TGF-β mRNA and TGF-β protein, and secrete significantly more fibronectin and proteoglycans (Okuda et al., supra). The rat nephritic model is relevant to human glomerulonephritis and glomerulosclerosis and in particular to human mesangial proliferative glomerulonephritis since it reproduces all the significant features of these human diseases (Yamamoto and Wilson, *Kidney Int.* 32:514–525 (1987); Bagchus et al., *Lab Invest.* 55:680–687 (1986) and Border, *Kidney Int.* 34:419–434 (1988)). Suppression of the production of extracellular matrix components and prevention of deleterious accumulation of mesangial matrix in glomeruli of glomerulonephritic rats was achieved by intravenous administration of neutralizing antibodies specific for TGF-β (Border et al *Nature* 346:371–374 (1990), which is incorporated herein by reference) or administration of purified decorin (see Example I and Border et al. *Nature* 360:361–364 (1992), which is incorporated herein by reference).

Glomerulosclerosis is considered to be a final common pathway leading to a progressive loss of renal function for a variety of diseases, including, for example, primary glomerulonephritis, diabetic nephropathy and lupus nephritis. These diseases are characterized by a common pathology involving mesangial cell proliferation and/or extracellular matrix expansion which is mediated, in part, by the action of TGF-β. As described herein, gene transfer of a nucleic acid encoding a TGF-β inhibitory agent into a cell in a subject can be used to reduce the pathology associated with glomerulosclerosis by inhibiting TGF-β-induced mesangial cell proliferation and deleterious accumulation of extracellular matrix in the kidney.

As described herein, the feasibility of the disclosed methods of the present invention was demonstrated in the acute mesangial proliferative model of glomerulonephritis induced by antithymocyte antiserum. Rats can be, for example, injected in the skeletal muscle with a nucleic acid encoding decorin. Since skeletal muscle is highly vascularized, decorin expressed by muscle cells enters the bloodstream and is delivered to other sites in the body where it associated with the extracellular matrix and inhibits the activity of TGF-β.

As used herein, the term, "nucleic acid encoding a TGF-β specific inhibitory agent" means a cDNA or a genomic DNA or an RNA encoding the TGF-β specific inhibitory agent. Decorin cDNA is an example of a nucleic acid encoding a TGF-β inhibitory agent.

The method of expressing an exogenous gene in vivo is defined herein by the term gene transfer. Gene transfer can be accomplished by direct injection of the nucleic acid encoding a TGF-β specific inhibitory agent in vivo, or by transfecting a cell ex vivo to obtain a cell expressing the agent which is then transplanted or grafted into the subject to be treated.

As used herein, the term "cell expressing a TGF-β specific inhibitory agent" means a cell that can produce and secrete the agent, which is encoded by the nucleic acid provided to the cell. A nucleotide sequence encoding a TGF-β specific inhibitory agent can be cloned into an expression vector where the sequence encoding the agent is operably linked with expression control elements. The pAct nucleic acid expression vector containing the human decorin nucleotide sequence operably linked to a constitutive promotor is a specific example of a nucleic acid encoding a TGF-β specific inhibitory agent. Expression control elements are well known in the art and include, for example, promoters, enhancers and appropriate start and stop codons.

The methods of decorin gene transfer also are useful for gene transfer of other TGF-β specific inhibitory agents. cDNA sequences or genomic sequences encoding the various agents of the present invention are useful for encoding the TGF-β specific inhibitory agent. Such sequences are known and available from publicly available DNA databanks and the genes can be cloned by PCR or be chemically synthesized. cDNA sequences known in the art include, for example, fibromodulin (Antonsson et al. *Biochem. Biophys. Acta.* 1774:204–206 (1993)), biglycan (Fisher et al., *J. Biol. Chem.* 264:4571–4578 (1989)) lumican (Blochberger et al., supra, 1992), betaglycan (Fukushima et al., *J. Biol. Chem.* 268:22710–22715 (1993) and Lopez-Casillas et al., *Cell* 67:785–795 (1991)) and endoglin (St-Jacques et al., *Endocrinology* 134:2645–2657 (1994)), each of which are incorporated herein by reference.

As used herein, "antibody" includes a full sized antibody molecule or a fragment such as Fab, F(ab')$_2$, Fv and Fd fragments that retain specific binding of the immunogen, such as TGF-β. Naturally occurring antibodies as well as non-naturally occurring antibodies and fragments of antibodies that retain binding activity are also an antibody as disclosed herein. Such non-naturally occurring antibodies can be constructed using solid phase peptide synthesis, or can be obtained, for example, by screening combinatorial libraries consisting of variable heavy chains and variable light chains as described by Huse et al., *Science* 246:1275–1281 (1989), which is incorporated herein by reference.

A monoclonal antibody specific for TGF-β that neutralizes the activity of TGF-β can be prepared from an immunized rodent or other animal using well known methods of hybridoma development as described, for example, by Harlow and Lane, *Antibodies: A laboratory manual* (Cold Spring Harbor Laboratory Press, 1988), which is incorporated herein by reference). TGF-β or a portion thereof can be used as an immunogen, which can be prepared from natural sources or produced recombinantly or can be chemically synthesized. Methods to identify hybridomas that produce monoclonal antibodies that function as a TGF-β specific inhibitory agent can utilize, for example, assays that detect inhibitors of binding between radiolabeled TGF-β and targets such as HepG2 cells or purified decorin (see Example I and WO 93/20202).

The cDNA sequences encoding the light and heavy chains of a monoclonal antibody specific for TGF-β can be obtained by cloning such sequences from hybridoma cells that secrete the antibody. Methods for cloning antibody genes are well known in the art (see, for example, Borrebaeck, *Antibody Engineering: A Practical Guide* (W. H. Freeman and Co., New York, 1991), which is incorporated herein by reference).

Humanized antibodies that inhibit the activity of TGF-β can be produced by grafting the nucleotide sequences encoding the complementarity determining regions (CDRs) from the rodent or other animal antibodies specific for TGF-β to nucleotide framework sequences derived from the light and heavy chain variable regions of a human immunoglobulin molecule. Human immunoglobulin variable region framework and constant region nucleotide sequences are well known in the art. A cDNA encoding a human immunoglobulin sequence can be obtained from publicly available gene repositories or can be cloned from human lymphoid cell lines also available from public cell repositories (see, for example, American Type Culture Collection, Rockville, Md.). Methods for humanizing antibodies by CDR grafting also are well known in the art (see, for example, Borrebaeck, supra, 1991; Reichmann et al., *Nature* 332:233 (1988); Queen et al. *Proc. Natl. Acad. Sci. (USA)* 86:10029 (1989), each of which are incorporated herein by reference). In addition, methods for using molecular modelling and mutagenesis approaches to maintain the original binding affinity and specificity of the rodent or other animal antibody when converted to a humanized form also are well known in the art (see, for example Borrebaeck et al., supra, 1991).

A variety of expression vectors and gene transfer methods useful for obtaining expression of a TGF-β specific inhibitory agent by gene transfer as disclosed herein are well known in the art (for example, see Sambrook et al., *Molecular Cloning: A laboratory manual* (Cold Spring Harbor Laboratory Press 1989); Kriegler M. *Gene Transfer and Expression: A Laboratory Manual* (W. H. Freeman and Co. New York, N.Y., 1990) and Wu, *Meth. in Enzymol,*

(Academic Press, New York, 1993), each of which is incorporated herein by reference). The choice of vector or method depends on several factors such as the particular TGF-β specific inhibitory agent and the amount of the agent required in a tissue to obtain a reduction in pathology. For example, the level of expression of a particular TGF-β specific inhibitory agent in a cell can depend on many factors, such as the nature of the cell, the regulatory regions operably linked to the nucleotide sequence encoding the agent as well as the agent itself. In addition, the level of expression of the TGF-β specific inhibitory agent that can be achieved in vivo in a tissue also depends on other factors such as the site of production in vivo and the pharmacokinetic properties of the agent.

Methods disclosed in the present invention are useful to help select the appropriate combination of factors, such as vector, regulatory regions, cell type to be transfected and method of gene delivery in order to achieve the necessary level of expression of a TGF-β specific inhibitory agent in a tissue desired by the practitioner. An in vitro transfection method disclosed herein provides the ability to evaluate parameters such as vector, regulatory elements and nature of the TGF-β specific inhibitory agent on expression by a particular cell. For example, the vector described in Example II, the pAct-Dec vector, which has a decorin encoded gene operably linked to the chicken β-actin constitutive promoter was initially tested by in vitro transfection of cultured muscle myocytes prior to attempting gene transfer to of skeletal muscle in vivo (see Example II).

The results disclosed herein show that skeletal muscle is a convenient and useful site for obtaining expression of a TGF-β specific inhibitory agent that can enter the blood and reduce a pathology at site distant from the muscle. Gene transfer methods suitable for the present invention also can be directed to cells other than muscle cells. Such cells include, for example, epithelial cells of particular organs. A higher concentration of the TGF-β specific inhibitory agent can be achieved in a particular tissue by directing the nucleic acid encoding the agent to a cell type localized within or near the tissue. Tissue specific expression control elements that enable selective cell type expression are known in the art and include, for example, the muscle creatine kinase enhancer for restricting expression to muscle cells or the immunoglobulin enhancer for restricting expression to B lymphoid cells.

A variety of methods can be used for introducing a nucleic acid encoding a TGF-β specific inhibitory agent into a cell at the site of injection in vivo. For example, the nucleic acid can be injected alone, can be encapsulated into liposomes or liposomes combined with a hemagglutinating Sendai virus, or can be encapsulated into a viral vector. In one embodiment, the nucleic acid was cloned into the pAct vector and the vector encapsulated into a liposome HVJ construct prior to injection.

Direct injection of a nucleic acid molecule alone or encapsulated, for example, in cationic liposomes also can be used for stable gene transfer of a nucleic acid encoding a TGF-β specific inhibitory agent into non-dividing or dividing cells in vivo (Ulmer et al., *Science* 259:1745–1748 (1993), which is incorporated herein by reference). In addition, the nucleic acid can be transferred into a variety of tissues in vivo using the particle bombardment method (Williams et al., *Proc. Natl. Acad. Sci. USA* 88:2726–2730 (1991), which is incorporated herein by reference).

Encapsulation of the nucleic acid into liposomes incorporating a Sendai virus that promotes cell fusion can be used for gene delivery of a nucleic acid of the present invention. In particular, the hemagglutinating virus of Japan is a Sendai virus (Z strain) that provides an effective means of achieving expression of a TGF-β specific inhibitory agent by transfecting cells by ex vivo and by in vivo methods (see Example II and III). The efficiency of gene transfer using the HVJ-liposome method was surprisingly better than with liposomes produced by Lipofectamine™ (see Example II and III).

Viral vectors are useful for gene transfer of a nucleic acid encoding a TGF-β specific inhibitory agent into a specific cell type in vivo or in vitro. Viruses are specialized infectious agents that can infect and propagate in specific cell types. This specificity for infecting particular cell types is especially suitable for targeting a TGF-β specific inhibitory agent to selected cells in vivo. The selection of a viral vector will depend, in part, on the cell type to be targeted.

Specialized viral vectors are well known in the art that can target to specific cell types. Such vectors include, for example, a vector derived from herpes simplex virus that targets neuronal cells (Battleman et al., *J. Neurosci.* 13:941–951 (1993), which is incorporated herein by reference), an immunodeficiency virus that targets hematopoietic cells (Carroll et al., *J. Cell. Biochem.* 17E:241 (1993), which is incorporated herein by reference), and recombinant adeno-associated viral vectors having general or tissue-specific promoters (Lebkowski et al. U.S Pat. No. 5,354,678, which is incorporated herein by reference). Recombinant adeno-associated viral vectors have the added advantage that the recombinant virus can stably integrate into the chromatin of even quiescent non-proliferating cells (Lebkowski et al., *Mol. Cell. Biol.* 8:3988–3996 (1988), which is incorporated herein by reference).

Viral vectors can be constructed to further control the type of cell that expresses the encoded TGF-β specific inhibitory agent by incorporating a tissue-specific promoter or enhancer into the vector (Dai et al., *Proc. Natl. Acad. Sci. USA* 89:10892–10895 (1992), which is incorporated herein by reference). A viral or other vector also can have the nucleotide sequence encoding the TGF-β specific inhibitory agent under control of a constitutive promoter. The pAct-Dec vector disclosed herein is an example of a constitutive expression vector useful for the present invention (see Example II).

Retroviral vectors are suitable for the methods of gene transfer disclosed herein. Such vectors can be constructed either to function as infectious particles or as non-infectious particles that undergo only a single initial round of infection. In the former case, the genome of the virus is modified so that it maintains the necessary genes, regulatory sequences and packaging signals to synthesize new viral proteins and RNA. However, genes conferring oncogenic potential of these viruses are destroyed or removed. After the viral proteins are synthesized, the host cell packages the RNA into new viral particles, which can undergo further rounds of infection. The viral genome also is engineered to encode and express the desired recombinant gene.

In the case of non-infectious viral vectors, a helper virus genome is required to provide the structural genes necessary to encode viral structural proteins. However, the helper virus is mutated to destroy the viral packaging signal required to encapsulate the helper viral RNA into viral particles. Thus, only the recombinant viral vector containing the gene of interest and a functional packaging signal, but lacking viral structural genes can be incorporated into a virus particle. Although this new virus can infect a target cell, no further infectious virus can be produced since there are no viral structural genes provided. Methods for constructing and using viral vectors are well known in the art and reviewed, for example, in Miller and Rosman, *Biotechniques* 7:980–990 (1992) and Davison and Elliot, *Molecular Virology: A Practical Approach* (IRL Press, New York, 1993), both of which are incorporated herein by reference).

A variety of vectors and promoters are available in the art to produce an expression vector that encodes for a TGF-β specific inhibitory agent. An important feature is that the promoter is functional in the desired cell type for expression and that the vector can be maintained in the cell for sufficient time to enable therapeutic benefit to the subject.

Receptor-mediated DNA delivery approaches also can be used to deliver a nucleic acid molecule encoding a TGF-β specific inhibitory agent into a cell in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference).

Gene transfer to obtain expression of the TGF-β specific inhibitory agent in a subject also can be performed by, for example, ex vivo transfection of autologous cells. Suitable cells for such ex vivo transfection include blood cells since these cells are readily accessible for manipulation and reintroduction back into the subject by methods well known in the art. Non-autologous cells such as allogeneic cells also can be used provided they share histocompatibility antigens with the subject to be treated.

Gene transfer of a TGF-β specific inhibitory agent by ex vivo transfection can be beneficial for obtaining high levels of expression since stable populations of cells can be selected for that express the agent. Moreover, expression levels can be increased further by incorporating drug selection markers into the vector which under the proper conditions result in the amplification of the encoded sequence. Such selection markers include, for example, dihydrofolate reductase or glutamine synthetase genes. Methods for gene selection and amplification in mammalian cells are well known in the art (see, for example, Sambrook et al. supra). Another approach for achieving high level expression of a TGF-β specific inhibitory agent is to perform multiple rounds of transfection and selection using vectors with different drug resistance genes.

Gene transfer through transfection of cells ex vivo can be performed by a variety of methods, including, for example, calcium phosphate precipitation, diethyaminoethyl dextran, electroporation, lipofection, or viral infection. Such methods are well known in the art (see, for example, Sambrook et al., supra and Wu, supra, 1993). Once the cells are transfected, they are then transplanted or grafted back into a subject to be treated. The cells once introduced into the body can produce the TGF-β specific inhibitory agent, which can enter the circulation and inhibit the activity of TGF-β at the site of the disease or condition.

The choice between gene transfer by in vivo and by ex vivo transfection can affect the choice of vector used for obtaining expression of a particular TGF-β specific inhibitory agent. For example, gene delivery of a neutralizing antibody to TGF-β requires separate expression of both the heavy and light chains of the antibody unless a single chain antibody design is used. If ex vivo transfection is chosen as the method of gene transfer and a genomic sequence is chosen for encoding the TGF-β specific inhibitory agent, then each chain of the antibody can be encoded by a different vector. In this case, expression of the complete antibody is achieved by separate sequential transfection of the two vectors or simultaneous transfection with both vectors and dual drug selection.

Gene transfer of a member of the decorin family of proteoglycans by direct injection of the encoding nucleic acid in vivo can be achieved by a single vector design. A single vector where both the heavy and the light chains of an antibody are encoded in the same vector, known as a dual chain vector, also can be used for expressing an antibody by gene transfer in vivo or ex vivo. Dual chain expression vectors, suitable for antibody expression are well known to those in the art (see, for example, Borrebaeck, supra 1991 and Phelps, et al. *J. Immunol.* 145:1200–1204 (1990), both of which are incorporated herein by reference). Alternatively, gene transfer of an antibody by direct injection of the nucleic acid in vivo can be achieved by introducing a mixture of two expression vectors, each encoding the immunoglobulin heavy or light chains of the antibody.

Various animal models of fibrotic diseases are well known in the art and are available for testing the efficacy of gene transfer using TGF-β specific inhibitory agents as disclosed herein. These include, for example, an acute rat antithymocyte serum model of mesangial proliferative glomerulonephritis (see Examples III and IV) and a chronic model of glomerular disease produced by repeated injections of antithymocyte serum (Yamamoto et al., supra). The chronic model produces progressive glomerular disease characterized by elevated levels of urinary protein, blood urea nitrogen and extracellular matrix. The chronic glomerulonephritic disease model is distinguished from the acute model in having progressive tubulointerstitial diease characterized by extracellular matrix accumulation.

Nephropathy also can be induced in animals by chronic administration of angiotensin II (Miller, et. al., *Amer. J. Physiol.* (Renal Fluid Electrolyte Physiol. 30:F549-F465 (1991), which is incorporated herein by reference. In this model, pumps delivering 100 ng angiotensin II/min (Alza Corp. Palo Alto, Calif.) in 0.01N acetic acid can be surgically implanted in the necks of rats to deliver angiotensin II and control rats can receive identical pumps containing 0.01N acetic acid. After 1 week of treatment, angiotensin treated rat glomeruli show a specific and substantial increase in TGF-β and collagen type I mRNA expression accompanied by an accumulation of extracellular matrix. This accumulation of matrix can be suppressed by intravenous administration of purified human decorin.

The streptozotocin rat model for human diabetic nephropathy also can be used to test the efficacy of gene transfer using TGF-β specific inhibitory agents. Diabetes can be induced in 150 g male Sprague-Dawley rats by a single intravenous injection of streptozotocin (Sigma hemical Co., St. Louis, Mo.), at 6.5 mg/100 g body weight n citrate buffer as described in Velasquez et al., *FASEB* 4:2850 (1990), Mauer et al., *Diabetes* 25:850 (1976) and U.S. application Ser. No. 07/885,674, each of which is incorporated herein by reference in their entirety.

The following examples are intended to illustrate but not limit the invention.

EXAMPLE I
Intravenous Administration of Purified Decorin

This example provides methods to use purified decorin to reduce a deleterious accumulation of extracellular matrix in an experimental model of glomerulonephritis. The amount of fibronectin present in glomeruli was used quantitatively to assess the ability of decorin to block matrix deposition in glomerulonephritis.

A. Purification of Decorin

Expression of Decorin

Decorin was produced using decorin-expressing CHO cells as follows. The 1.8 kb full-length decorin cDNA described in Krusius and Ruoslahti (supra, 1986), was used for the construction of decorin expression vectors. For the expression of decorin core protein, cDNA was mutagenized so the fourth codon, TCT, coding for serine, was changed to ACT coding for threonine, or GCT coding for alanine. This was engineered by site-directed mutagenesis according to the method of Kunkel (*Proc. Natl. Acad. Sci USA* 82:488 (1985)), which is incorporated herein by reference. The presence of the appropriate mutation was verified by DNA sequencing.

The mammalian expression vectors pSV2-decorin and pSV2-decorin/CP-thr4 core protein were constructed by ligating the decorin cDNA or the mutagenized decorin cDNA into 3.4 kb HindIII-Bam HI fragment of pSV2 (Mulligan and Berg, *Science* 209:1423 (1980), which is incorporated herein by reference).

Dihydrofolate reductase (dhfr)-negative CHO cells (CHO-DG44) were cotransfected with pSV2-decorin or pSV2-decorin/CP and pSV2dhfr by the calcium phosphate coprecipitation method. The CHO-DG44 cells transfected with pSV2-decorin are deposited with the American Type Culture Collection under Accession Number ATCC No. CRL 10332. The transfected cells were cultured in nucleoside-minus alpha-modified minimal essential medium ($\alpha$-MEM), (GIBCO, Long Island) supplemented with 9% dialyzed fetal calf serum, 2 mM glutamine, 100 units/ml penicillin and 100 $\mu$g/ml streptomycin. Colonies arising from transfected cells were picked using cloning cylinders, expanded and checked for the expression of decorin by immunoprecipitation from $^{35}SO_4$-labeled culture supernatants. Clones expressing a substantial amount of decorin were then subjected to gene amplification by stepwise increasing concentration of methotrexate (MTX) up to 0.64 $\mu$M (Kaufman and Sharp, *J. Mol. Biol.* 159:601 (1982), which is incorporated herein by reference). All the amplified cell lines were cloned either by limiting dilution or by picking single MTX resistant colonies. Stock cultures of these established cell lines were kept in MTX-containing medium. Before use in protein production, cells were subcultured in MTX-minus medium from stock cultures and passed at least once in this medium to eliminate the possible MTX effects.

Alternatively, larger scale productions of decorin were performed using CHO cells attached to microcarrier beads. Decorin-expressing CHO cells as described above were allowed to adhere to microcarrier beads, then were cultured in suspension. Once a seed culture of decorin-expressing cells was established, the fermentation reaction vessel was seeded and the growth phase of fermentation continued until the desired cell density was achieved. At that time, fresh medium was slowly perfused into the reactor vessel and conditioned medium was collected at a rate of about 80–85% of the reactor volume per day. Care was taken to separate cell-containing microcarriers from the perfusate so as not to lose decorin-producing cells. The harvest medium was incubated at 4° C. for 24 hours prior to filtration to allow cell debris to settle out.

Decorin was purified from 40 liters of CHO cell culture medium produced in microcarrier cultures. A solution of benzamidine and $Na_4EDTA$ was added to a final concentration of 1× in the medium (100× solution is 100 mM benzamidine and 500 mM $Na_4EDTA$). The medium was filtered with Whatman #1 filter paper and the NaCl concentration was adjusted to 0.4 NaCl.

Purification of Decorin

A Q-Sepharose column was prepared by washing 300 ml resin (Q-Sepharose fast flow gel; Pharmacia, Piscataway, N.J.) in a fritted disc glass funnel with 10 column volume deionized water to remove ethanol. The Q-Sepharose was degassed and placed into a 10 cm×30 cm column with a flow adapter (Watson/Marlow Peristaltic Pump with 9.6 mm ID tubing). The bubble trap and pump were connected to the column, which then was equilibrated at a flow rate of 200 ml/min with 10 column volume buffer A (25 mM Tris, pH 7.8, 0.4M NaCl). UV absorbance at 280 nm, 1.0 AUFS (Absorbance units, full scale) was determined; the detector was set to zero using buffer A.

Cell culture medium was loaded onto the column at a flow rate of 200 ml/min and the flow through was collected. The column was washed with buffer A ((1 liter). The column was eluted with buffer B ((1.5 liter) 25 mM Tris, pH 7.8, 1M NaCl) and one minute fractions were collected. The eluted peak was pooled, the volume was recorded (usually 1–1.5 liters) and absorbance at 280 nm and at 260 nm was determined. The latter reading was used to detect nucleic acid co-eluted with decorin on the Q-Sepharose column. One volume (equal to the pooled volume) 2M guanidinium-HCl (GuHCl) was added and the sample was loaded onto an Octyl-Sepharose column.

The Octyl-Sepharose column was prepared by washing 60 ml Octyl-Sepharose gel (Pharmacia) with 10 column volume deionized water in a sintered glass funnel to remove EtOH. The gel was degassed and placed in a 2.6 cm×30 cm water jacketed column with two flow adapters (Pharmacia), which compacted and retained the gel in position. The column was maintained at 25° C. with a refrigerated circulator. The UV monitor (280 nm) was connected and was set to zero with buffer C ((10 column volume or 600 ml) 0.1 NaOAc, pH 6.3, 1M GuHCl; filtered with 0.2 $\mu$M acetate filter and degassed).

The fraction collected from the Q-Sepharose column was loaded onto the Octyl-Sepharose column at a flow rate of 3 ml/min and samples were collected at 2 min/fraction (6 ml/tube). The column was washed with buffer C, until the baseline was established, then with buffer D (0.1M NaOAc, pH 6.3, 2M GuHCl; filtered with 0.2 $\mu$M acetate filter, then degassed) until the same baseline was established.

Decorin was eluted using buffer E ((200 ml) 0.1M NaOAc, pH 6.3, 3M GuHCl) at a flow rate of 3 ml/min. A small amount of protein contaminant eluted with the decorin. An elution profile was performed on the fractions by determining the absorbance at 280 nm and 260 nm to show that most of O.D. 280 absorbance was due to decorin and not to nucleic acid. The column then was eluted using buffer F ((150 ml) 0.1M NaOAc, pH 6.3, 4M GuHCl; filtered with 0.2 $\mu$M acetate filter, then degassed), to remove an unidentified 200 kDa protein and some histone proteins. The column was stripped with of buffer G ((150 ml) 0.1M NaOAc, pH 6.3, 8M GuHCl; filtered with 0.2 $\mu$M acetate filter, then degassed) to remove more host cells contaminating proteins.

The 3M GuHCl fraction containing decorin was diluted 1:10 with a solution containing 50 mM $NaPO_4$ at pH 7.4. A Q-Sepharose column (Pharmacia) was equilibrated with a buffer, 50 mM $NaPO_4$ (pH 7.4), 0.4M NaCl, and the diluted decorin solution was pumped (Minipuls 2 peristaltic pump with 1.52 ID PVC manifold tubing; Gilson; Middleton Wis.) onto the column at a rate of 3 ml/min. The column was washed with five column volumes of the same buffer, then decorin was eluted with additional buffer, 50 mM $NaPO_4$ (pH 7.4)/1.0M NaCl. The eluant was concentrated/diafiltered by ultrafiltration (Amicon Inc., Beverly, Mass.).

Assay for Decorin

Human recombinant decorin produced from by the above recombinant and purification procedures was detected and quantified using a direct decorin ELISA as follows. Immulon-2 flat bottom plates were coated with dilutions of a decorin standard and unknown samples. Dilutions were made in 0.1M $HCO_3$ ((500 mls) 1.38 g $Na_2CO_3$; 3.11 g $NaHCO_3$; volume brought up with $ddH_2O$; the pH checked at 9.6; the solutions filtered, sterilized, and stored at 4° C.), pH 9.6, in borosilicate glass tubes and each set was plated immediately after dilution. Concentration of the decorin standard set started at 19 ng/ml and was serially diluted 1:1.5 down to 1.7 ng/ml. Samples of unknown decorin concentration were diluted to fall somewhere along the standard curve, usually for purified decorin the dilution range was $1\times10^5$ to $16\times10^5$ as two-fold dilutions. The volume used was 100 μl/well. Plates were incubated at 4° C. overnight and sealed.

The coating solution was flicked out and 200 μl 1× PBS+1% BSA ((100 mls) 90 ml $ddH_2O$; 10 ml 10× PBS ((1 liter) 80 g NaCl; 2 g KCl; 6.1 g Na2HPO4; 2 g KH2PO4; volume brought up with ddH2O); 1 g Bovine Serum Albumin; solution made fresh the day of the assay) was added per well and incubated at 37° C. for 0.5–1.0 hours. The wells were then washed three times with 1× PBS+0.1% Tween-20.

A 100 μl/well aliquot of rabbit anti-decorin antibody (anti-PG40 (described in WO 91/10727 obtained from La Jolla Cancer Research Foundation) at 1:1000) was added. The antibody was diluted in 1× PBS+0.1 BSA+0.1% Tween-20 ((100 mls) 90 ml $ddH_2O$; 10 ml 10× PBS; 0.1 g Bovine Serum Albumin; 0.1 ml Tween-20; solution made fresh the day of the assay) and incubated at 37° C. for 60 minutes. The wells were washed three times with 1× PBS+0.1% Tween-20 ((1 liter) 900 ml $ddH_2O$; 100 ml 10× PBS; 1 ml Tween-20; solution made fresh the day of the assay).

A 100 μl/well of GoatαRb-Horse Radish Peroxidase (BioRad (Richmond, Va.) or Promega Tustin, Calif.) diluted 1:3000 with 1× PBS+0.1% BSA+0.1% Tween-20 was added and incubated at 37° C. for 60 minutes. The wells were then washed five times with 1× PBS+0.1% Tween-20. Two hundred μl per well of freshly made o-phenylenediamine dihydrochloride (OPD) solution (25 mls 0.1M Citrate Phosphate Buffer ((500 mls) 5 g citric acid; 7 g $Na_2HPO_4$ (anhydrous); volume brought up with $ddH_2O$, pH checked at 5.0; filtered, sterilized and stored at 4° C.); 1 10 mg OPD tablet (Sigma); 6 μl 30% $H_2O_2$) was then added and incubated at room temperature in the dark for 15 minutes. Fifty microliters per well of 7.8 $H_2SO_4$ (55 mls 36M $H_2SO_4$; 200 mls distilled water) was added to stop the reaction. The data was read at OD 490 and analyzed using a linear fit of the data. The highest points of the curve were eliminated if the assay started to "top out."

Three lots of decorin samples prepared by the above recombinant and purification procedures contained 0.82 mg/ml, 1.23 mg/ml, and 1.43 mg/ml of decorin.

B. Binding Assays to Measure the Activity of TGF-β Specific Inhibitory Agents

Binding of $^{125}$I-TGF-β to HepG2 cells

About $2.5\times10^4$ HepG2 cells (ATCC #HB8025) were incubated with 250 pM $^{125}$I-TGF-β, in the presence of recombinant human decorin (DC-12) or PT-71 (maltose binding protein) for 2 hours at room temperature. Cells were washed with washing buffer (128 mM NaCl, 5 mM KCl, 5 mM $Mg_2SO_4$, 1.2 mM $CaCl_2$, 50 mM HEPES, pH 7.5) four times before determination of bound counts per minute (cpm).

Table I provides numerical data for decorin (DC-12) inhibition of TGF-β binding to HepG2 cells. The "% Change" represents the difference in the mean cpm of the test samples compared to the cpm of the medium (negative control). The α-TGF-β antibody inhibits the binding of labeled TGF-β to cells bearing TGF-β receptors and serves as a positive control.

Binding $^{125}$I-TGF-β to Immobilized Decorin

A 96-well Linbro microtiter plate was coated with 0.5 μg/ml recombinant decorin at 50 μl/well. The plate was placed in a 37° C. incubator overnight and thereafter washed 3 times with 200 μl PBS (0.15M NaCl) per well to remove unbound decorin. TGF-β labeled with $^{125}$I (400 pM, New England Nuclear, Bolton-Hunter Labeled)

TABLE I

BINDING OF 125I-TGF-β1 TO HEPG2 CELLS

| Treatment | Concentration | CPM Bound | Mean | % Change |
|---|---|---|---|---|
| Medium* | — | 13,899** | | |
| | | 13,898 | | |
| | | 12,529 | | |
| | | 11,764 | | |
| | | 12,694 | | |
| | | 12,448 | 12,872 ± 856 | — |
| TGF-β1 | 2.5 × 10E-8M | 3,092 | | |
| | | 2,543 | | |
| | | 2,800 | 2,812 ± 275 | −78 |
| Anti-TGF-β1 (R&D) | 2.5 × 10E-7M | 6,191 | | |
| | | 4,848 | | |
| | | 3,839 | 4,959 ± 1,180 | −61 |
| Decorin (DC-12) | 2.5 × 10E-6M | 2,745 | | |
| | | 2,844 | | |
| | | 1,945 | 2,511 ± 493 | −80 |
| | 2.5 × 10E-7M | 4,258 | | |
| | | 5,914 | | |
| | | 4,052 | 4,741 ± 1,021 | −63 |
| | 2.5 × 10E-8M | 13,596 | | |
| | | 12,798 | | |
| | | 11,599 | 12,664 ± 1,005 | −2 |
| PT-71 | 2.5 × 10E-6M | 11,859 | | |
| | | 13,129 | | |
| | | 12,348 | 12,449 ± 636 | −3 |
| | 2.5 × 10E-7M | 11,259 | | |
| | | 11,022 | | |
| | | 9,343 | 10,541 ± 1,045 | −18 |
| | 2.5 × 10E-8M | 10,886 | | |
| | | 10,778 | | |
| | | 10,104 | 10,589 ± 424 | −18 |

*25,000 HepG2 cells obtained from subconfluent cultures were incubated with 250 pM 125I-TGF-β1 and TGF-β, anti TGF-β, decorin, or decorin fragments for 2 hours at room temperature.
**Unbound 125I-TGF-β1 was separated from bound by washing cells 4×.

was pre-incubated with or without competitors in 200 μl PBS/0.05% Tween-20 for 1 hour, 45 minutes at room temperature. Competitors included recombinant human decorin preparation DC-12, and the decorin fragment, PT-71 as a negative control.

Fifty μl/well of the pre-incubated TGF-β mixture or control were added and incubated overnight at 0° C. Following the incubation, 50 μl of the free TGF-β supernatants were transferred to labeled tubes. The plate was washed 3 times with 0.05% Tween-20 in PBS (200 μl/well). Reducing sample buffer (2× Laemmli sample buffer) was added at 100 μl/well and incubated at 37° C. for 30 minutes. While gently pulsing the solution, 100 μl of bound $^{125}$I-TGF-β was removed from each well and transferred into tubes for counting in a gamma counter. The 50 μl free TGF-β samples were counted in parallel to the 100 μl bound TGF-β samples to obtain the bound:free ratio. The results in Table 1 show that TGF-β1, anti-TGF-β1 or decorin inhibit the binding of radiolabelled TGF-β to its receptor on HepG2 cells.

C. Tissue Staining

Fluorescein isothiocyanate-conjugated sheep anti-human fibronectin was from the Binding Site, Inc. (San Diego, Calif.). Immunofluorescence staining for fibronectin was scored without knowledge of the source of the tissue using a 0 to 4 scale (0=no staining, 4=maximal strong staining) in 20 glomeruli selected at random in coded sections prepared from each animal. Differences between groups were analyzed by a test described by Okuda et al., (supra).

Glomeruli were stained with antibodies that detect EDA+ fibronectin and tenascin; these matrix components are relatively specifically induced by TGF-$\beta$ Mouse monoclonal antibody prepared against human fibronectin containing extra domain A (EDA+), was kindly provided by Dr. L. Zardi, Instituto Nazionale per la Ricerca sul Cancro, Italy. Rabbit anti-human tenascin was obtained from Telios Pharmaceuticals, Inc. (La Jolla, Calif.). Fluorescein isothiocyanate-conjugated rat F(ab')2 anti-mouse IgG and donkey F(ab')2 anti-rabbit IgG were used as second antibodies (Jackson Immunoresearch Lab, West Grove, Pa.). The technique of matrix scoring and the method of statistical analysis for EDA+ fibronectin and tenascin staining are the same as for fibronectin, which is described above.

D. Treatment of Glomerulonephritic Rats with Decorin

Glomerulonephritis was induced in Sprague-Dawley rats (4–6 wk old) by intravenous injection of antithymocyte serum as described by Okuda, et al., (supra). Age matched rats served as normal controls. Eight rats were divided into four groups of two each and injected with antithymocyte serum. One hour later treatment was begun with a single intravenous injection of 0.45 mg of recombinant human decorin or bovine decorin in 0.5 ml of PBS or, as control, 0.5 ml PBS alone (rats were restrained but not anesthetized for the injections). Treatment was continued with a single daily injection of decorin or PBS as follows: Decorin was administered to Group 1 for two days, Group 2 for four days and Group 3 for six days. Group 4 received PBS alone for six days. When decorin was discontinued in Groups 1 and 2, PBS was substituted so that all animals received six daily injections. All treatment was stopped on day 7, a 24 h urine was collected, after which the animals were sacrificed and the kidneys were removed.

An experiment was conducted, according to the protocol described above, to test the control preparations as follows: Eight rats were injected with antithymocyte serum, divided into groups of two rats each, and injected daily for six days with 0.5 ml of PBS alone or PBS containing aggrecan, ovalbumin, bovine serum albumin. The carbohydrate content of aggrecan and decorin were determined and aggrecan in PBS was injected at the same carbohydrate concentration as decorin. An additional four rats received a single injection of PBS instead of antithymocyte serum and served as normal controls. All animals were sacrificed following a 24 h urine collection as described above and urinary protein and creatinine were measured as described by Okuda et al., (supra).

For all techniques, kidneys were perfused in situ with cold PBS and then excised. Kidney tissue was prepared for light and immunofluorescence microscopy as described by Okuda et al., (supra).

The results showed that four or six daily injections of recombinant decorin or bovine decorin suppressed fibronectin deposition to a level not significantly different from that found in the normal rats. Control injections consisted of buffer alone, a different proteoglycan and two proteins. A cartilage proteoglycan, aggregan, was used as a negatively charged molecule to control for the glycosaminoglycan chain of decorin; aggregan does not inhibit TGF$\beta$, as described by Yamaguchi et al., supra, 1990). Ovalbumin was used as a control for the core protein of decorin because both proteins are approximately the same molecular size. Serum albumin was used as an unrelated protein control. Proteoglycan and protein controls were indistinguishable from glomerulonephritic rats injected with buffer alone. Two injections of decorin given early in the disease process also had no effect on the fibronectin accumulation.

EDA+ fibronectin and tenascin were detectable in only trace amounts in glomeruli of normal rats. However, EDA+ fibronectin and tenascin were greatly increased in nephritic glomeruli in rats treated with no or two injections of decorin. However, as was the case with whole fibronectin, four or six injections of decorin greatly reduced the deposition of these two markers of TGF-$\beta$ activity. Histological analysis of periodic acid-Schiff stained sections of the same kidneys showed a comparable effect of decorin in preventing the increase in glomerular extracellular matrix and associated glomerular enlargement that occurs in the disease.

Decorin given for four or six days also suppressed the development of proteinuria. The ratio or urinary protein concentration to the urinary concentration of creatinine was used to assess proteinuria because this method minimizes the influence of differences in urinary volume on the protein excretion values, as described by Ginsberg et al., supra. Mean values for normals, disease controls, low dose decorin (two injections) and high dose decorin-treated rats (four and six injections) were respective 0.7, 15.2, 14.8 and 2.4 ($p<0.01$ for high dose decorin rats compared to disease controls).

These results show a dramatic effect of intravenous decorin administration in preventing the deposition of extracellular matrix in injured glomeruli from nephritic rats. Previously it was shown that the accumulation of extracellular matrix in glomerulonephritis is caused by overproduction of TGF-$\beta$ (Okuda et al., supra, Border et al., supra, 1990). That matrix accumulation in this model was prevented by the injection of decorin demonstrates an in vivo activity of decorin in suppressing TGF-$\beta$.

EXAMPLE II

Expression of Decorin in Cultured Myocytes

This example provides a method to evaluate expression of decorin in muscle cells in vitro.

The rat decorin expression vector, pAct-Dec, was constructed by cloning the EcoRI fragment containing the complete region of rat decorin cDNA from vector pGEM4-RNDCN (Aundi and Dreher et al. *Eur. J. Cell. Biol.* 59:314–321 (1992) and Dreher et al. *Eur. J. Cell Biol.* 53:296–304 (1990), both of which are incorporated herein by reference) into the expression vector pAct-CAGGS (Niwa et al. *Gene* 108:193–200 (1991), which is incorporated herein by reference). The expression vector, pAct-CAT, which is the same vector as pAct-Dec except that decorin cDNA is replaced with the bacterial gene encoding chloramphenicol acetyl-transferase (CAT), was produced as described previously (Kaneda et al. *Science* 243:375–378 (1989) and Isaka et al. *J. Clin. Invest.* 92:2597–2601, (1993), each of which is incorporated herein by reference).

C2C12 cultured mouse myocyte cells (American Type Cell Culture Collection, Rockville, Md.) were seeded at $1\times10^6$ cells per well in six-well culture plates and grown to subconfluence (70–80% confluent) in Dulbecco's minimal essential medium containing 10% fetal calf serum (culture medium). The cells were transfected with either pAct-Dec or pAct-CAT by the hemagglutinin virus of Japan (HVJ)-liposome method (Kato et al. *J. Biol. Chem.* 266:3361–3364, (1991), which is incorporated herein by reference) or by lipofection with Lipofectamine™ (Gibco BRL, Gaithersburg, Md.) as described previously (Takeshita et al. *J. Clon. Invest.* 93:652–651 (1993), which is incorporated herein by reference).

The HVJ is a Sendai virus, which promotes membrane fusion. Methods that employ the functional capacity of HVJ can alternatively be used to promote liposome fusion with recipient cells. HVJ-liposomes were produced by dissolving chromatographically pure bovine brain phosphatidylserine (sodium salt; Avanti Polar Lipids Inc.) in tetrahydrofuran and 0.01 m $K_2PO_4$, pH 6.8 (9:1, v/v). Phosphatidylcholine and cholesterol (both from Sigma, St. Louis, Mo.) were each dissolved in tetrahydrofuran. Phosphatidylserine, phosphatidylcholine and cholesterol were mixed in a weight ratio of 1:4.8:2. The lipid mixture (10 mg) was deposited on the sides of a flask by removal of the organic solvent in a rotary evaporator, and the residue was stored at -20° C. under nitrogen gas.

HVJ (Z strain) was propagated in chorioallantoic fluid of embryonated eggs (Nakanishi et al., *Exp. Cell Res.* 159:399–409 (1991), which is incorporated herein by reference). HVJ was collected by centrifugation at 27,000×g for 40 min. and suspended with BSS(-). The HVJ suspension was layered on a discontinuous gradient composed of 60, 40, and 30% sucrose (1:1:8, v/v) in BSS(-). The gradient was centrifuged at 60,000×g for 4 hr at 4° C., and the HVJ was stored at 4° C.

HVJ was inactivated by 11 $J.m^{-2}.s^{-1}$ of UV irradiation for 3 min just before use. The hemagglutinating activity of HVJ was determined as described previously (Salk et al., *J. Immunol.* 69:87–97 (1944), which is incorporated herein by reference). One $A_{540}$ of HVJ suspension contained 1 mg/ml protein and was equivalent to 15,000 hemagglutinating units (HAU)/ml.

The liposome suspension (0.5 ml, containing 10 mg of lipids) was mixed with HVJ (64,000 HAU) in a total volume of 4 ml of BSS(-). The mixture was incubated at 4° C. for 30 min. and then at 37° C. for 2 hr with gentle shaking. To prevent formation of multinuclear cells, free HVJ was removed from the HVJ-liposomes by sucrose density gradient centrifugation. The suspension was layered onto a discontinuous sucrose gradient (1 ml of 60%, 1 ml of 40%, and 8 ml of 30% sucrose in BSS(-) and centrifuged at 60,000×g at 4° C. for exactly 3.5 hr in a swing-bucket rotor. A 4 ml fraction from the top of each centrifuge tube was collected.

On day 7 after transfection, the cells were washed three times with balanced salt solution (BSS(-): 140 mM NaCl, 5.4 mM KCl, 10 mM Tris-HCl, pH 7.6) and then incubated with 1 ml of HVJ-liposome solution (2.5 mg of lipids and 10 μg encapsulated DNA) at 4° C. for 5 min. followed by 37° C. for 30 min. The cells were washed with BSS(-), fed fresh culture medium and further incubated at 37° C.

For lipofection, 50 μg of plasmid DNA dissolved in 500 μl of Optimen™ serum-free medium (BRL Life Technologies, Gaithersburg, Md.) was added to 250 μl of Lipofectamine™ (BRL Life Technologies) previously dissolved in 250 μl of water. The mixture was incubated for 30 min. at room temperature (rt) and then added dropwise to a cell culture well containing the myocytes in 2 ml of serum-free medium. The cells were incubated for 2 hr at 37° C. to allow uptake of the DNA. After incubation, the medium was removed, the cells were washed in BSS(-), fresh culture medium was added and the cells were incubated further at 37° C.

For both the HVJ and the lipofection methods, the culture medium was replaced on the day following transfection and twice each week therafter. Cells were removed from the wells and passaged by distribution of the cells into two new wells at weekly intervals.

The transfected cells were biosynthetically labeled on day 3, 7 and 14 following transfection. Cells were washed 3× with sterile phosphate buffered saline (PBS; 0.14M NaCl, 2 mM KCl, 10 mM $Na_2HPO_4$, 1.8 mM $KH_2PO_4$, pH 7.4) and then culture medium without methionine, cysteine, glutamine and fetal calf serum was added. Cells were incubated for 2 hr at 37° C. The medium was removed from the cells and replaced with fresh culture medium containing 100 μCi/ml $^{35}$S-sulfate (New England Nuclear, Boston, Mass.) and the cells were incubated for 18 hr at 37° C., after which the culture medium was removed.

The culture media containing radiolabeled proteoglycans was analyzed by sodium dodecyl sulfate polyacrylamide gel electrophoresis (SDS-PAGE) on a 4–12% acrylamide gel under non-reducing conditions as described previously (Okuda et al. *J. Clin. Invest.* 86:453–462 (1992), which is incorporated herein by reference). After SDS-PAGE, the gel was dried and exposed to X-ray film using standard methods (see, for example, Harlow and Lane, supra, 1988). The autoradioraphic exposure was scanned using a densitomiter (LKB instruments Bromma, Sweden) to obtain a relative estimate of decorin production by the tranfected cells.

Figure 1:
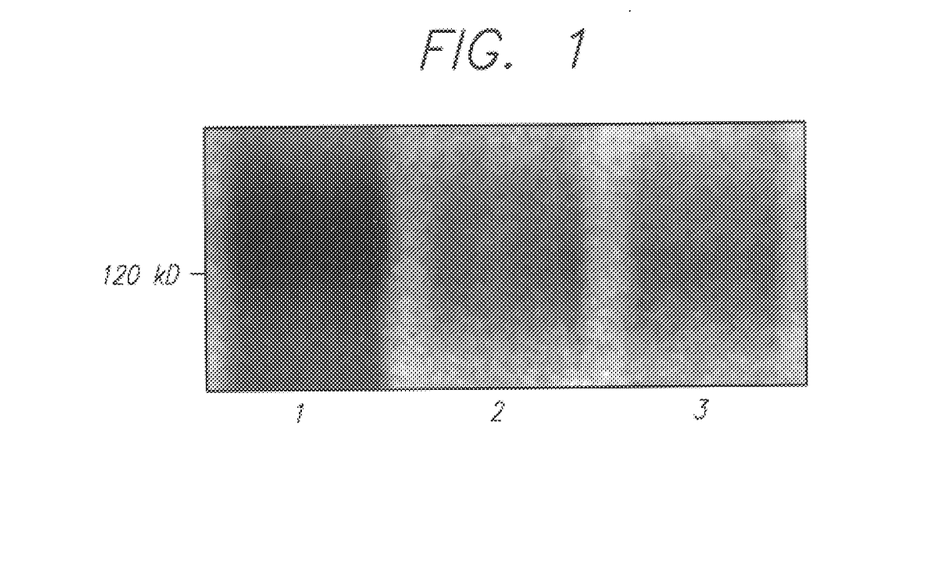
FIG. 1 is an autoradiograph which shows that rat decorin can be synthesized and secreted from cultured mouse myocytes following transfection with a decorin expression vector. The decorin expression vector was encapsulated in liposomes incorporating the hemagglutinating virus of Japan (HVJ-liposomes; lane 1) or in lipofectamine™ (lane 2). Lane 3 represents transfection with a chloramphenicol acetyl transferase expression vector encapsulated in HVJ-liposomes. The position for decorin is indicated by the marker at left. kD: kilodaltons.

Myocytes transfected with pAct-Dec in conjunction with the HVJ-liposome method secreted 9 fold more decorin into the culture medium (see 120 kD marker) than did myocytes transfected with pAct-Dec in conjunction with Lipofectamine™. In addition, decorin expression following transfection with pAct-CAT in HVJ-liposomes was similar in amount to the level of decorin expressed using pAct-Dec and Lipofectamine™ (FIG. 1). The results indicate that transfection of pAct-Dec is much more effective when conducted with the HVJ-liposome method than by lipofection with Lipofectamine™ (FIG. 1).

EXAMPLE III

Expression of Decorin In Vivo by Transfection of Skeletal Muscle

This example provides a method to evaluate the efficiency of decorin expression in vivo following intramuscular injection of a decorin expression vector.

Figure 2:
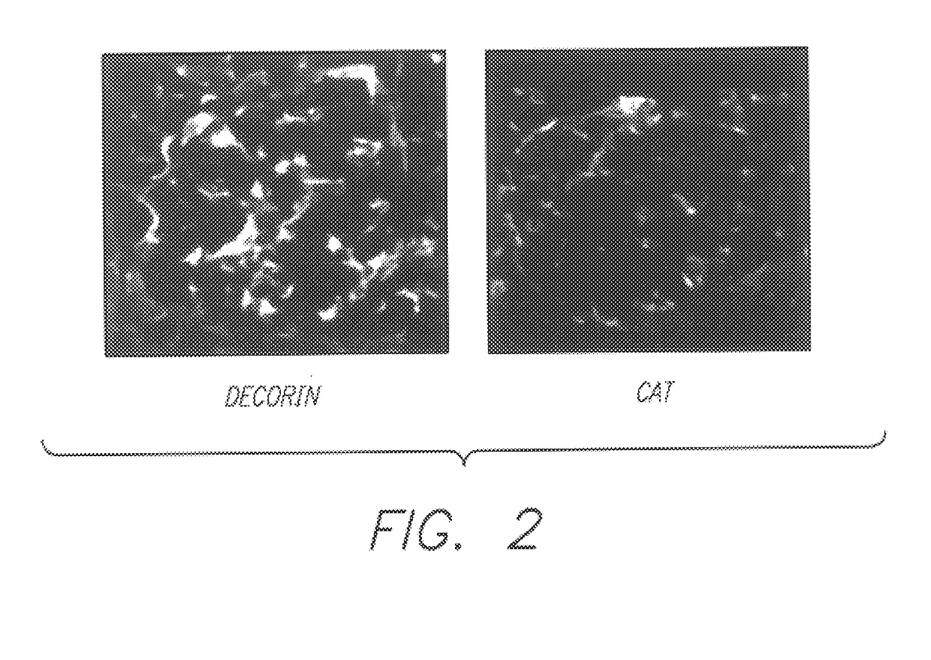
FIG. 2 are immunofluorescence micrographs, which show increased decorin in rat kidney glomeruli following intramuscular injection of a decorin expression vector. Immunofluorescence for decorin was performed on sections of kidney from a rat sacrificed 5 days after intramuscular injection of a decorin expression vector (labelled decorin) or a chloramphenicol acetyl-transferase expression vector (labelled CAT).

For in vivo transfection, 8 ml of BSS(-) was added to 2 ml of HVJ-liposome solution (5 mg of lipids and 20 μg encapsulated DNA) and the solution was centrifuged at 15,000 rpm for 30 min. The pelleted liposomes were concentrated by resuspension with 0.4 ml of BSS(-) containing 1 mM $CaCl_2$. Approximately 0.2 ml of the concentrated HVJ liposomes containing the plasmid DNA were injected through a 27 gauge needle into four sites of exposed gluteal muscles of 150 g male Sprague-Dawley rats anesthetized with methoxyflurane. Each muscle received two injections of 0.1 ml. On days 3, 5, 7, 10 and 14 after injection, rats were sacrificed and kidney, liver and lung tissue were removed. Tissues were quickly snap-frozen in cold isopentane, and approximately 5 micron sections cut using a cryostat. Tissue sections were fixed in acetone for 10 min. prior to adding primary rabbit antibodies to detect human decorin (Mann et al. *J. Biol. Chem.* 265:5317–5323 (1990) which is incorporated herein by reference). The binding of the primary rabbit antibodies were detected by staining with fluorescein isothiocyanate coupled donkey antibodies specific for rabbit IgG (Jackson Labs, West Grove, Pa.).

pAct-Dec treated rats showed increased staining for decorin in kidney, liver and lung compared to pAct-CAT control vector treated rats at all time points evaluated (see FIG. 2 for day 5 post injection). The expression of immunoreactive decorin in the pAct-Dec treated animals was similar overall to the results obtained when purified decorin is administered intravenously (see Border et al. supra, 1992). The results indicate that introducing a decorin expression vector into skeletal muscle results in the expression of decorin that can enter the blood and access other organs such as kidney, lung and liver. The level of decorin expressed in the blood of decorin transfected rats was below detection by decorin ELISA indicating that high serum concentrations are not required for decorin to enter the circulation and accumulate in the various different tissues.

EXAMPLE IV
Effect of Decorin Gene Delivery in vivo on the Development of Nephritis in an Experimental Animal Model This example provides methods to evaluate the effect of administering a decorin expression vector on the development of pathology in an experimental animal model of fibrosis that involves TGF-$\beta$-induced abnormal accumulation of extracellular matrix components.

A. Effect on Expression of TGF-$\beta$ mRNA and Protein

Four rats in each of 2 groups were transfected by intramuscular injection with pAct-Dec or pAct-CAT as described in Example III. The following day, the rats were injected intravenously with 0.25 ml of sheep anti-rat thymocyte serum to generate nephritis as described previously (see Okuda et al., supra, and Application WO 91/04748, which is incorporated herein by reference in its entirety). Six days after disease induction, rats were anesthetized, kidneys were perfused, then removed and processed to isolate the glomeruli, which were pooled within each group. Total RNA was prepared from glomeruli and northern blotting was performed as previously described (Okuda et al. supra, and Yamamoto et al. *Kidney Int.* 45:916–927 (1994), both of which are incorporated herein by reference). A probe for TGF-$\beta$1 was generated by subcloning a 280 base pair Pvu II fragment from a mouse TGF-$\beta$1 cDNA (Derynck et al., *J. Biol. Chem.* 261:4377–4379 (1986), which is incorporated herein by reference) into Hinc II digested pBluescript SKII+ (Strategene, San Diego, Calif.). A rat GAPDH cDNA was obtained as previously described (Fort et al., *Nucl. Acid Res.* 13:1431–1443 (1985), which is incorporated herein by reference). The density of autoradiographic bands representing decorin mRNA at 2.5 kb and GAPDH mRNA at 1.3 kb) was determined by standard densitometry scanning with a laser densitomiter (LKB). GAPDH band density was used as a control for RNA loading as described previously (Yamamoto et al., supra).

Immunofluorescence microscopy was performed as described in Example III on frozen sections of rat kidney taken 6 days after disease induction. TGF-$\beta$ immunoreactive cells were identified by staining with a rabbit polyclonal antibody to human TGF-$\beta$1 (King Brewing Co., Ltd, Kakagawa, Japan). Fluorescein isothiocyanate-conjugated donkey F(ab')$^2$ anti-rabbit IgG was used a secondary antibody (Jackson Immunoresearch Labs). Glomerular TGF-$\beta$01 positive cells were counted by scoring 30 randomly selected glomeruli as previously described (Okuda et al. supra, and Yamamoto et al. supra).

Figure 3A:
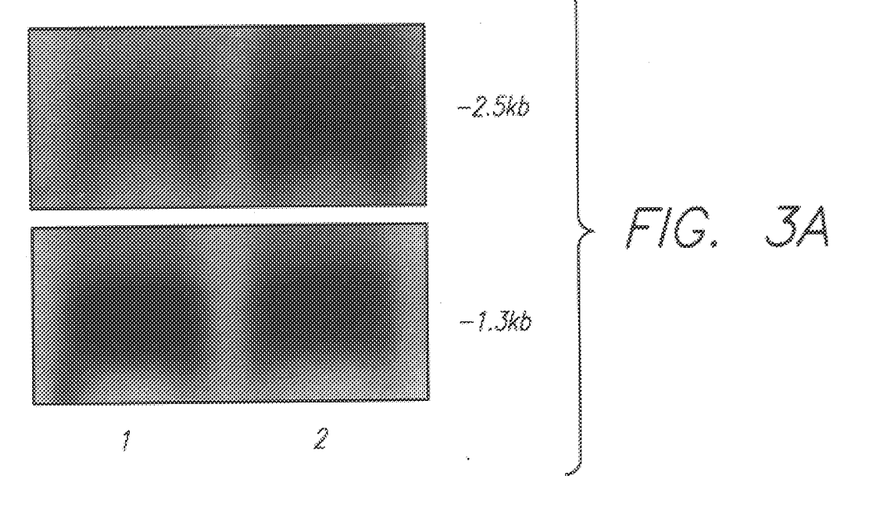
Figure 3B:
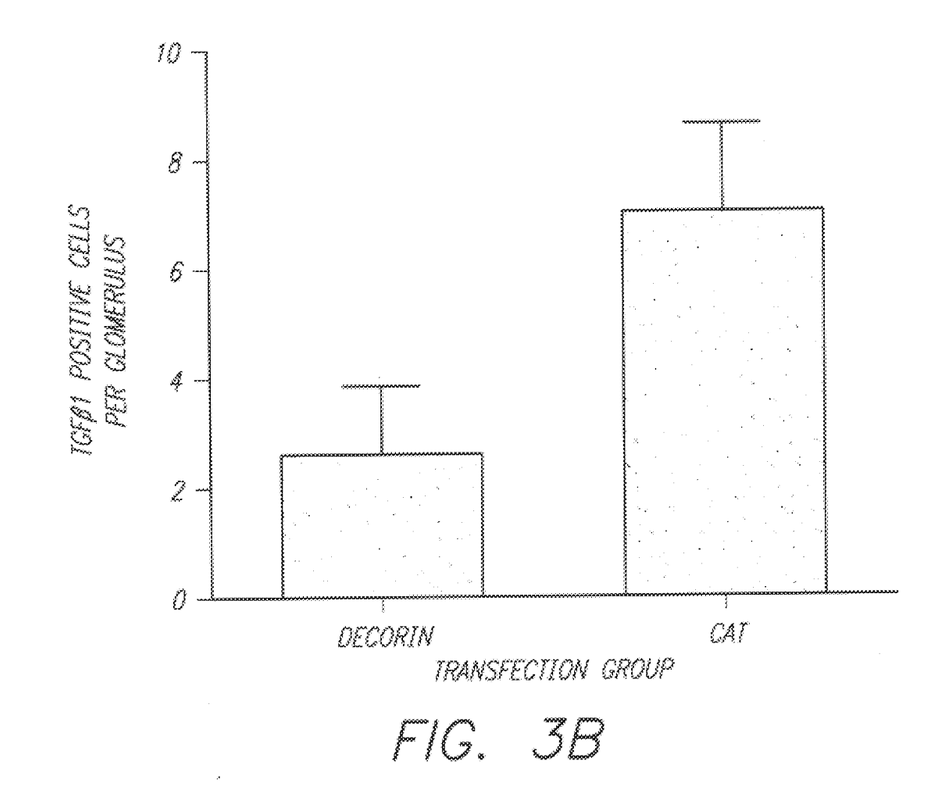
FIG. 3B is a summary of TGF-β immunoreactive cells in glomeruli from nephritic rats sacrificed 7 days after intramuscular injection of a decorin expression vector (labelled decorin) or a chloramphenicol acetyl-transferase expression vector (labelled CAT). Values are mean ± the standard deviation.

On day 6 post induction of disease, glomerular TGF-$\beta$1 mRNA levels in pAct-Dec transfected rats were suppressed to 37% of those in glomeruli from disease-induced animals transfected with the pAct-CAT control vector (FIG. 3A). Glomerular TGF-$\beta$1 positive cells were significantly fewer in pAct-Dec transfected nephritic rats compared to that of the pAct-CAT control vector (2.5±1.6 vows. 7.0±2.7; Decorin vows. CAT, p<0.01; FIG. 3B).

B. Effect on Accumulation of Extracellular Matrix Components and Kidney Function Transfection of rat skeletal muscle in vivo with pAct-Dec and pAct-CAT and disease induction were as described above. Four rats for each condition were sacrificed at either 6 or 14 days post disease induction. These time points were chosen because in this disease model, TGF-$\beta$1 mRNA expression peaks by day 6 and matrix component accumulation peaks by day 14 prior to returning to control levels. The day 6 time point also included a control group that was not disease induced and received a single injection of PBS.

Formalin fixed and frozen kidney tissue sections were processed for periodic acid-Schiff staining and identification of immunoreactive collagen types I and II, fibronectin EDA+ and tenascin as previously described (Okuda et al. supra, and Yamamoto et al. supra). Tissue sections were fixed in acetone as described and stained for the presence of collagen types I and III, fibronectin EDA+ and tenascin. Primary polyclonal rabbit antibodies specific for rat collagen types I and III (kindly provided by Dr. A. Ohshima, Wakayama Medical College) were produced as described previously (Takahara et al., *Lab. Invest.* 59:509 (1988), which is incorporated herein by reference). Polyclonal rabbit antibodies to tenascin were obtained commercially (Gibco/BRL) as well as a mouse monoclonal antibody specific for fibronectin EDA+ (Accurate Chemical Scientific Corp., Westbury, N.Y.) that was produced as previously described (Balza et al., *FEBS Letters* 228:42–44 (1988), which is incorporated herein by reference). Secondary antibodies were fluorescently labelled rat F (ab')$^2$ anti-mouse IgG (Jackson Immunoresearch Labs.) for mouse and as described above for rabbit.

PAS staining for total extracellular matrix proteoglycans and individual extracellular matrix components were evaluated by scoring 30 randomly selected glomeruli per sample on a 0 to 4 scale as previously described (Yamamoto et al., supra 1994).

Figure 4A:
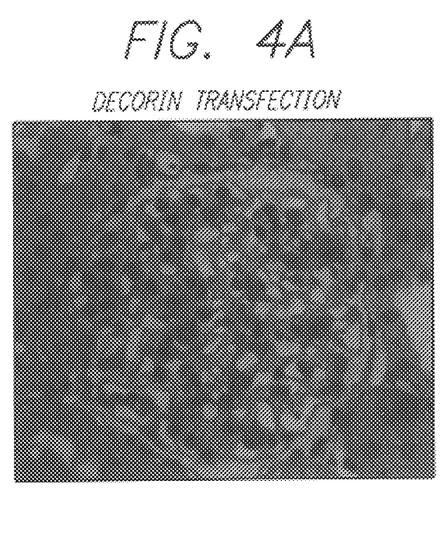
FIGS. 4A and 4B show a periodic acid-Schiff (PAS) stain of a section of kidney from a nephritic rat injected 6 days earlier with a decorin expression vector (labelled Decorin transfection) or a chloramphenicol acetyl-transferase (CAT) expression vector (labelled CAT transfection), respectively. The dark areas of the section indicate PAS staining.
Figure 4B:
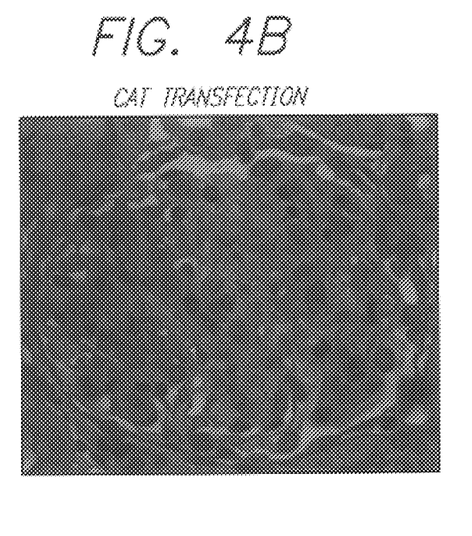
Figure 4C:
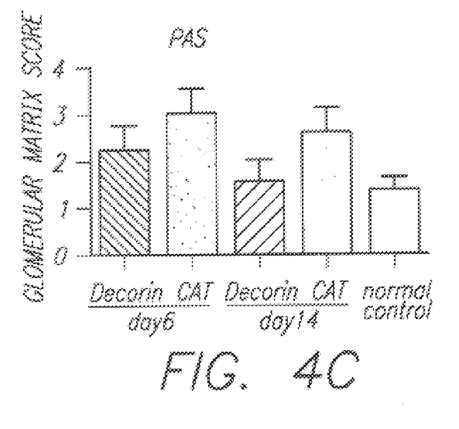
FIGS. 4C to 4F show a summary of glomerular cell expression of immunoreactive EDA+ fibronectin (4.D.), collagen type I (4.E.) or tenascin (4.F.) or staining by periodic acid-Schiff (PAS; 4.C.) in normal rats and in nephritic rats injected previously with a decorin expression vector or a CAT expression vector. Day 6 and day 14 indicate the time after disease induction that kidneys were removed. Values are mean ± the standard deviation.
Figure 4D:
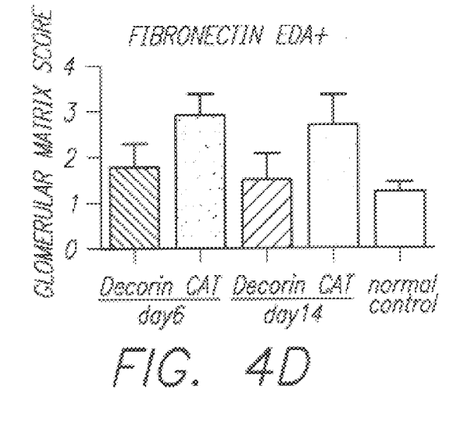
Figure 4E:
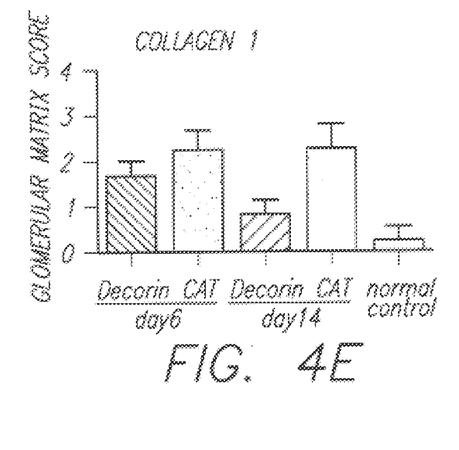
Figure 4F:
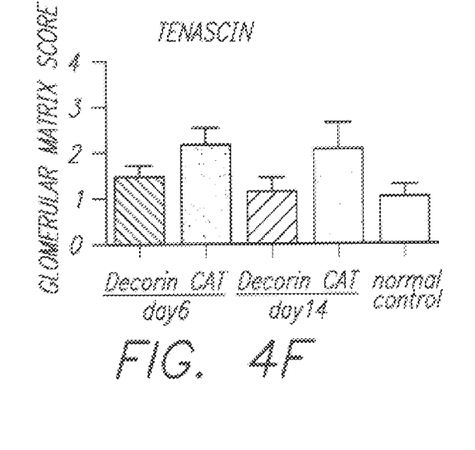

PAS staining of decorin transfected kidney tissue sections on day 6 post disease induction showed a decreased accumulation of total extracellular matrix proteoglycans as compared to that of CAT transfected rats (FIGS. 4A and 4B). Quantitation of individual extracellular matrix positive cells and PAS positive cells showed that decorin transfection significantly reduced the accumulation of extracellular matrix materials for EDA+ fibronectin, tenascin and collagen I and III at both time points after disease induction relative to control CAT transfected rats (p<0.01; decorin vows. CAT transfected; FIG. 4, collagen III data not shown). The score for detectable PAS, EDA+ fibronectin, tenascin positive cells at 14 days post disease-induction in decorin transfected rats was not significantly different from the normal PBS injected rats, while deposition in CAT transfected animals remained significantly elevated (p<0.01). These results show that administration of a decorin expression vector in the skeletal muscle of rats that subsequently develop acute nephritis can block the accumulation of extracellular matrix components that result in fibrosis of the kidney.

Proteinuria, a hallmark of the clinical severity of glomerulonephritis, was significantly reduced in the decorin transfected rats on day 6 (mg/day, mean±SD; decorin vows. CAT) (17.3±5.5 vows. 118±52.4, p<0.01) and on day 14 (21.9±7.7 vows. 89.5±19.6, p<0.01). Proteinuria that occurs in this model on days 1–3 is due to injection of anti-thymocyte serum that causes lysis of a portion of the glomerular mesangial cells. This early proteinuria was not decreased by decorin transfection 24 hours before (83.1±27.6 vows. 102.2±23.1. N.S.) or 24 hours after disease induction (data not shown). This result indicates that transfection did not affect immunological injury to the glomeruli but likely acted by preventing the deleterious accumulation of extracellular matrix induced by TGF-β1 overproduction.

Although the invention has been described with reference to the presently-preferred embodiments, it should be understood that various modifications can be made without departing from the spirit of the invention. Accordingly, the invention is limited only by the claims that follow.

I claim:

1. A method for reducing deleterious accumulation of TGF-β induced extracellular matrix in tissue of a subject, said method comprising:
    (a) introducing into the subject a heterologous nucleic acid encoding a TGF-β inhibitory agent selected from the group consisting of a proteoglycan, a TGF-β receptor, an anti-TGF-β antibody, a fragment of the proteoglycan, a fragment of the TGF-β receptor, and a fragment of the anti-TGF-β antibody, where each agent has the TGF-β inhibitory function of reducing deleterious accumulation of TGF-β induced extracellular matrix; and
    (b) expressing in cells in said subject the introduced nucleic acid encoding the TGF-β inhibitory agent and secreting the TGF-β inhibitory agent encoded by the introduced nucleic acid for a time and under conditions effective to produce an amount of the TGF-β inhibitory agent effective to reduce the deleterious accumulation of extracellular matrix material in said tissue of a subject where deleterious accumulation of extracellular matrix material induced by TGF-β occurs.

2. The method of claim 1, wherein said TGF-β specific inhibitory agent is first introduced into a cell ex viva to obtain a cell expressing the TGF-β specific inhibitory agent and the cell expressing said agent is transplanted into said subject.

3. The method of claim 1, wherein said cell is selected from the group consisting of a skeletal muscle cell, a kidney cell, a lung cell, a liver cell and a skin cell.

4. The method of claim 1, wherein said deleterious accumulation of extracellular matrix is associated with a condition in the subject selected from the group consisting of glomerulonephritis, ARDs, cirrhosis of the livers, fibrotic cancer, fibrosis of the lungs, post myocardial infarction, cardiac fibrosis, post-angioplasty restinosis, renal interstitial fibrosis, scarring or a diabetes-associated pathology.

5. The method of claim 1, wherein said tissue is selected from the group consisting of kidney, liver, lung and skin tissue.

6. A method for reducing the accumulation of extracellular matrix associated with glomerulonephritis in a subject comprising:
    a) introducing into the subject a heterologous nucleic acid encoding a TGF-β inhibitory agent selected from the group consisting of a proteoglycan, a TGF-β receptor, an anti-TGF-β antibody, a fragment of the proteoglycan, a fragment of the TGF-β receptor, and a fragment of the anti-TGFβ antibody, where each agent has the TGF-β inhibitory function of reducing deleterious accumulation of TGF-β induced extracellular matrix; and
    (b) expressing in cells in said subject the introduced nucleic acid encoding the TGF-β inhibitory agent and secreting the TGF-β inhibitory agent encoded by the introduced nucleic acid for a time and under conditions effective to produce an amount of the TGF-β inhibitory agent effective to reduce accumulation of extracellular matrix material induced by TGF-β in the kidney and suppress glomerulonephritis.

7. The method of claim 1 or claim 6, wherein said TGF-β specific inhibitory agent is selected from the group consisting of decorin, biglycan, fibromodulin, lumican, betaglycan and endoglin, and fragments thereof having TGF-β inhibitory action.

* * * * *